United States Patent
Kwik et al.

(10) Patent No.: US 11,798,682 B2
(45) Date of Patent: Oct. 24, 2023

(54) ELECTROSURGICAL SYSTEM, ELECTROSURGICAL INSTRUMENT, METHOD FOR READING CONFIGURATION DATA, AND ELECTROSURGICAL SUPPLY DEVICE

(71) Applicant: OLYMPUS WINTER & IBE GMBH, Hamburg (DE)

(72) Inventors: Anne Kwik, Berlin (DE); Lutz Kersten, Berlin (DE); Thilo Vahldiek, Potsdam (DE); Christian Schröder, Berlin (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 210 days.

(21) Appl. No.: 17/172,900

(22) Filed: Feb. 10, 2021

(65) Prior Publication Data

US 2021/0249123 A1    Aug. 12, 2021

(30) Foreign Application Priority Data

Feb. 10, 2020    (DE) .................... 10 2020 103 280.3

(51) Int. Cl.
  *G16H 40/40*    (2018.01)
  *G16H 20/40*    (2018.01)
  (Continued)

(52) U.S. Cl.
  CPC ......... *G16H 40/40* (2018.01); *A61B 18/1206* (2013.01); *G16H 20/40* (2018.01); *A61B 2018/00994* (2013.01)

(58) Field of Classification Search
  CPC .... G16H 40/40; G16H 20/40; A61B 18/1206; A61B 2018/00994
  See application file for complete search history.

(56) References Cited

U.S. PATENT DOCUMENTS

| | | |
|---|---|---|
| 2004/0044339 A1 | 3/2004 | Beller et al. |
| 2004/0044641 A1 | 3/2004 | Saliba |

(Continued)

FOREIGN PATENT DOCUMENTS

| | | |
|---|---|---|
| DE | 100 57 585 A1 | 5/2002 |
| DE | 10 2013 202526 A1 | 8/2014 |

(Continued)

OTHER PUBLICATIONS

Jul. 2, 2021 Search Report issued in European Patent Application No. 21151962.4.

(Continued)

*Primary Examiner* — Aryan E Weisenfeld
(74) *Attorney, Agent, or Firm* — Oliff PLC

(57) ABSTRACT

An electrosurgical system includes: an electrosurgical supply device, and an electrosurgical instrument, wherein the electrosurgical instrument includes a memory element which can be read out by the electrosurgical supply device when the electrosurgical instrument is connected to the electrosurgical supply device, and configuration data is stored on the memory element, which can be evaluated by the electrosurgical supply device in order to configure operating parameters which are compatible with the electrosurgical instrument. The electrosurgical system is characterized in that the configuration data is arranged in a flexible data structure which allows the memory element to simultaneously store multiple sets of configuration data which can be read and evaluated by different types of electrosurgical supply devices.

14 Claims, 4 Drawing Sheets

Figure 1:
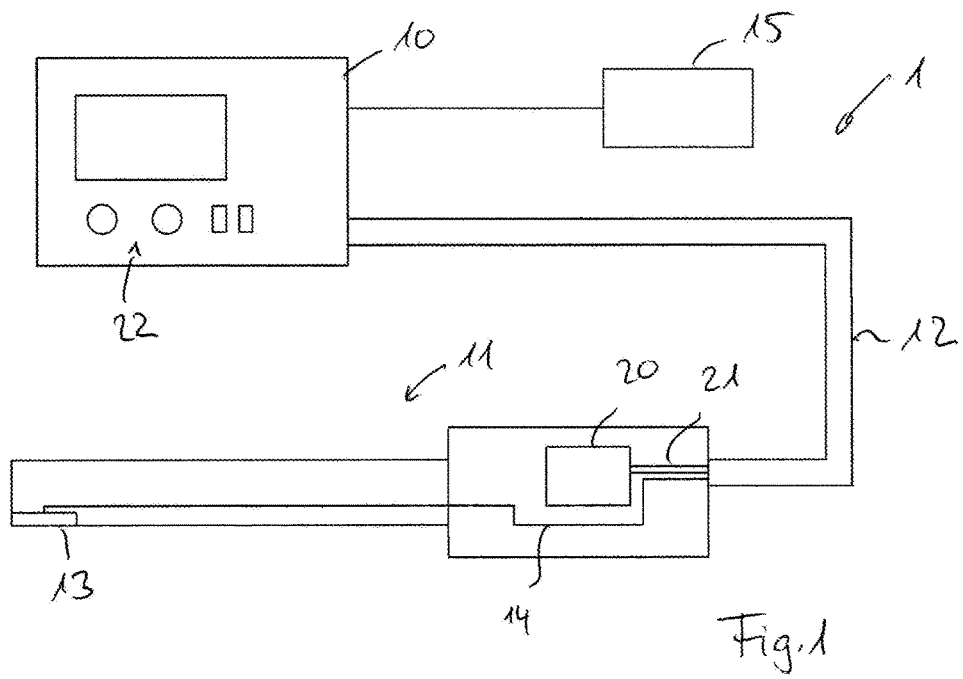

(51) Int. Cl.
*A61B 18/12* (2006.01)
*A61B 18/00* (2006.01)

(56) References Cited

U.S. PATENT DOCUMENTS

| | | | |
|---|---|---|---|
| 2009/0248007 | A1 | 10/2009 | Falkenstein et al. |
| 2012/0109448 | A1 | 5/2012 | Maas et al. |
| 2013/0046292 | A1 | 2/2013 | Janssen et al. |
| 2016/0015446 | A1 | 1/2016 | Assmus et al. |
| 2016/0220299 | A1* | 8/2016 | Maser ............ A61B 90/90 |
| 2017/0315808 | A1 | 11/2017 | Boeddeker et al. |

FOREIGN PATENT DOCUMENTS

| | | |
|---|---|---|
| DE | 10 2015 201470 A1 | 7/2016 |
| DE | 102016108081 A1 | 11/2017 |
| DE | 10 2018 103 957 A1 | 9/2019 |
| EP | 0363863 A2 | 4/1990 |
| EP | 1 337 194 B1 | 12/2008 |
| EP | 3 506 278 A1 | 7/2019 |
| JP | H09-073417 A | 3/1997 |
| JP | 2011-526157 A | 10/2011 |
| WO | 02/041798 A1 | 5/2002 |
| WO | 2009/124097 A1 | 10/2009 |
| WO | 2011/000533 A1 | 1/2011 |

OTHER PUBLICATIONS

Jan. 4, 2022 Office Action issued in Japanese Patent Application No. 2021-008252.
Jul. 7, 2021 extended Search Report issued in European Patent Application No. 21151963.2.
Sep. 6, 2022 Office Action issued in Japanese Patent Application No. 2021-008253.
Dec. 5, 2020 Office Action issued in German Patent Application No. 10 2020 103 278.1.
Dec. 4, 2020 Office Action issued in German Patent Application No. 10 2020 103 280.3.
U.S. Appl. No. 17/172,733, filed Feb. 10, 2021 in the name of Kersten et al.

* cited by examiner

ELECTROSURGICAL SYSTEM, ELECTROSURGICAL INSTRUMENT, METHOD FOR READING CONFIGURATION DATA, AND ELECTROSURGICAL SUPPLY DEVICE

The invention relates to an electrosurgical system comprising an electrosurgical supply device, and an electrosurgical instrument, wherein the electrosurgical instrument comprises a memory element which can be read out by the electrosurgical supply device when the electrosurgical instrument is connected to the electrosurgical supply device, and configuration data is stored on the memory element which can be evaluated by the electrosurgical supply device in order to configure operating parameters which are compatible with the electrosurgical instrument. Furthermore, the invention relates to an electrosurgical instrument of a corresponding electrosurgical system, a method for reading configuration data, and an electrosurgical supply device.

Electrosurgical systems are being used in surgery for a some time to perform various procedures. In electrosurgery in the narrower sense, tissue to be treated is directly exposed to electric currents, which are usually high-frequency alternating currents. By appropriately dimensioning the instruments and the currents and voltages used, different tissue effects may be achieved, such as coagulation or cutting of the tissue. In order to reliably achieve a desired tissue effect, it is necessary that an electrosurgical signal emitted by an electrosurgical supply device, for example a high-frequency generator, is correctly calibrated to the electrosurgical instrument used. Otherwise, the tissue effect may be inadequate or even endanger the patient or the attending physician.

Systems are also known in which a tissue to be treated is additionally or exclusively subjected to an ultrasound sonotrode. In this case, there is usually a transducer in the instrument to be used, which converts an electrical signal provided by a supply device in the form of an ultrasound generator into ultrasonic oscillations of the sonotrode. Such ultrasound systems are also considered to be electrosurgical systems in terms of the invention. Also, for such corresponding systems, it is important that the electrical signal provided by the supply device is matched to the instrument in order to ensure proper functioning of the instrument.

In modern electrosurgical systems, the instrument is equipped with a memory element on which configuration data for the supply device is stored.

When the instrument is connected to the supply unit, the supply unit reads the configuration data from the memory element and configures the emitted electrical signal accordingly. Additional user settings on the supply unit may be possible or necessary in the process.

In the continuous further development of electrosurgical systems, the effect occurs that the development of supply devices on the one hand and instruments on the other hand follow different development cycles. Newly developed instruments should be able to use the full range of functions of current supply units, but at the same time they should also be able to be operated with older supply units.

For the design of the configuration data, the problem arises that complete downward compatibility, i.e. compatibility with supply devices of older design, can usually only be achieved with losses in the full utilization of new available functionalities.

It is therefore a subject of the invention to provide an electrosurgical system which is improved with respect to the described problem.

According to a first aspect of the invention, this subject is achieved by an electrosurgical system comprising: an electrosurgical supply device, and an electrosurgical instrument, wherein the electrosurgical instrument comprises a memory element that can be read out by the electrosurgical supply device when the electrosurgical instrument is connected to the electrosurgical supply device, and configuration data is stored on the memory element that can be evaluated by the electrosurgical supply device, in order to configure operating parameters which are compatible with the electrosurgical instrument, which is characterized in that the configuration data is arranged in a flexible data structure which allows the memory element to simultaneously store multiple sets of configuration data which can be read and evaluated by different types of electrosurgical supply devices.

Different types of electrosurgical supply devices include, among others, different generations of supply devices.

The flexible data structure in which the configuration data is organized opens up the possibility of storing, on the one hand, a set of configuration data which is compatible with a supply device of an older generation and, on the other hand, a second set of configuration data which is compatible with a supply device of a more recent, or the latest, generation.

The term "flexible data structure" is to be understood in the sense of the invention in such a way that the position, structure, and/or length of the individual sets of configuration data are not rigidly predetermined, but are determined in particular by the content of data elements of the configuration data itself.

In a possible further development of an electrosurgical system according to the invention, the flexible data structure may comprise a first set of configuration data stored at a fixed predetermined memory address of the memory element, and the flexible data structure may further comprise a second set of configuration data stored at a second memory address of the memory element which is dependent on the length of the first set of configuration data. With such a data structure, it may be achieved that a supply device of an older generation, which expects only a single set of configuration data at a predetermined address of the memory element, may access the first set of configuration data. Accordingly, the second set of configuration data is stored after the first set of configuration data and can only be read by supply devices of a newer design which can read sets of configuration data from different addresses of the memory element.

A set of configuration data may have a fixed predetermined length. Preferably, this may be the first set of configuration data.

At least one set of configuration data may have a flexible length, and may comprise a length data element indicating the length of the corresponding set of configuration data. In this way, it is possible to stack multiple sets of configuration data in a quasi-sequential manner in the memory element, where a supply device can determine the address of the next set of configuration data in each instance from the address of the current set and the contents of the length data element.

The length data element itself may also directly contain the address of the next set of configuration data.

In an advantageous development of an electrosurgical system according to the invention, the data structure may comprise a termination data element indicating the end of the data structure. This may prevent the supply device from attempting to access a set of configuration data that is not present. In doing so, memory access errors could otherwise occur which would impair the operation of the electrosurgical system.

The data structure may provide, for at least one set of configuration data, a memory area that cannot be operationally overwritten.

Preferably, the data structure may provide, for at least one set of configuration data, a writable memory area, and the electrosurgical supply device may be configured to store operational data in the writable memory area.

In particular, for electrosurgical instruments designed for only a limited number of applications, for example, the number of applications already performed, energy/power delivered, timestamps, or similar information may be stored in the writable memory area. The supply device can then read this data before reenabling the instrument and decide whether reuse of the instrument is permissible.

Here, the writable memory area may comprise two operational data elements, and the electrosurgical supply device may be configured to store operational data alternately in one of the two operational data elements. Thereby, the previously stored value of the operational data is still available even after a failed writing operation, which may be caused, for example, by electrical interference.

The object is achieved according to a second aspect of the invention by an electrosurgical instrument of an electrosurgical system according to the above embodiments. With respect to the achievable advantages and effects herein, reference is explicitly made to the above description.

According to a third aspect of the invention, the object is achieved by a method for reading configuration data of an electrosurgical instrument in an electrosurgical system according to the above embodiments, comprising the steps of: (a) determining an address at which a first set of configuration data is stored, (b) reading a set of configuration data from the determined address, (c) determining an address at which a next set of configuration data is expected, (d) checking whether a termination data element is stored at the address determined in step (c), and (e) repeating steps (b) to (d) until a termination data element is detected at the determined address.

By means of the described method, an electrosurgical supply device can sequentially read all sets of configuration data stored in the memory element of the electrosurgical instrument. The supply device may then consider a single, multiple, or all sets of configuration data to configure the electrical signal to be delivered.

In a possible further development of a method according to the invention, before step d), it may be checked whether data is stored at the determined address, and the method may be terminated if no data is stored at the determined address. In this way, problems which may arise when reading configuration data from the memory element of an instrument of older design can be avoided.

The problem is solved according to a fourth aspect of the invention by an electrosurgical supply device of an electrosurgical system, which is configured to perform a method according to the above.

The invention is described in more detail below with reference to a number of exemplary figures, wherein the embodiments shown in the figures are merely intended to assist in a better understanding of the invention without limiting it.

There are shown in:
FIG. 1: an electrosurgical system,
FIG. 2: a data structure,
FIG. 3: a structure of a set of configuration data,
FIG. 4: a method for reading and writing operational data,
FIG. 5: a method for reading configuration data.

FIG. 1 shows an electrosurgical system 1 with an electrosurgical supply device 10 which is a high frequency generator, and with an electrosurgical instrument 11. The electrosurgical instrument 11 is connected to the electrosurgical supply device 10 via a cable 12. Instead of the depicted cable 12, the connection between the electrosurgical instrument 11 and the electrosurgical supply device 10 can also be made contactless, for example using NFC (Near Field Communication) or RFID (Radio Frequency Identification).

At a distal end of the electrosurgical instrument 11, an electrode 13 is disposed with which tissue may be treated. For this purpose, the electrode 13 is connected to the electrosurgical supply device 10 via a line 14.

The electrosurgical instrument may have more than one electrode. Alternatively or in addition to the electrode 13, the electrosurgical instrument 10 may comprise one or more ultrasound transducers.

The electrosurgical supply device 10 generates a high frequency electrical signal, which is conducted via the line 14 to the electrode 13 where it applies a therapeutic effect to tissue not shown. To complete the electrosurgical circuit, a neutral electrode 15 may be provided, which is also connected to the electrosurgical supply device 10.

The electrosurgical instrument 11 is equipped with a memory element 20 on which configuration data is stored. Once the electrosurgical instrument 11 is connected to the electrosurgical supply device 10, the electrosurgical supply device 10 reads out the memory element 20 via lines 21. The electrosurgical supply device 10 uses the configuration data read from the memory element 20 to configure the electrical signal that is delivered to the electrosurgical instrument 11. Different characteristics of the electrical signal may also be altered by control elements 22 on the electrosurgical supply device 10.

Figure 2:
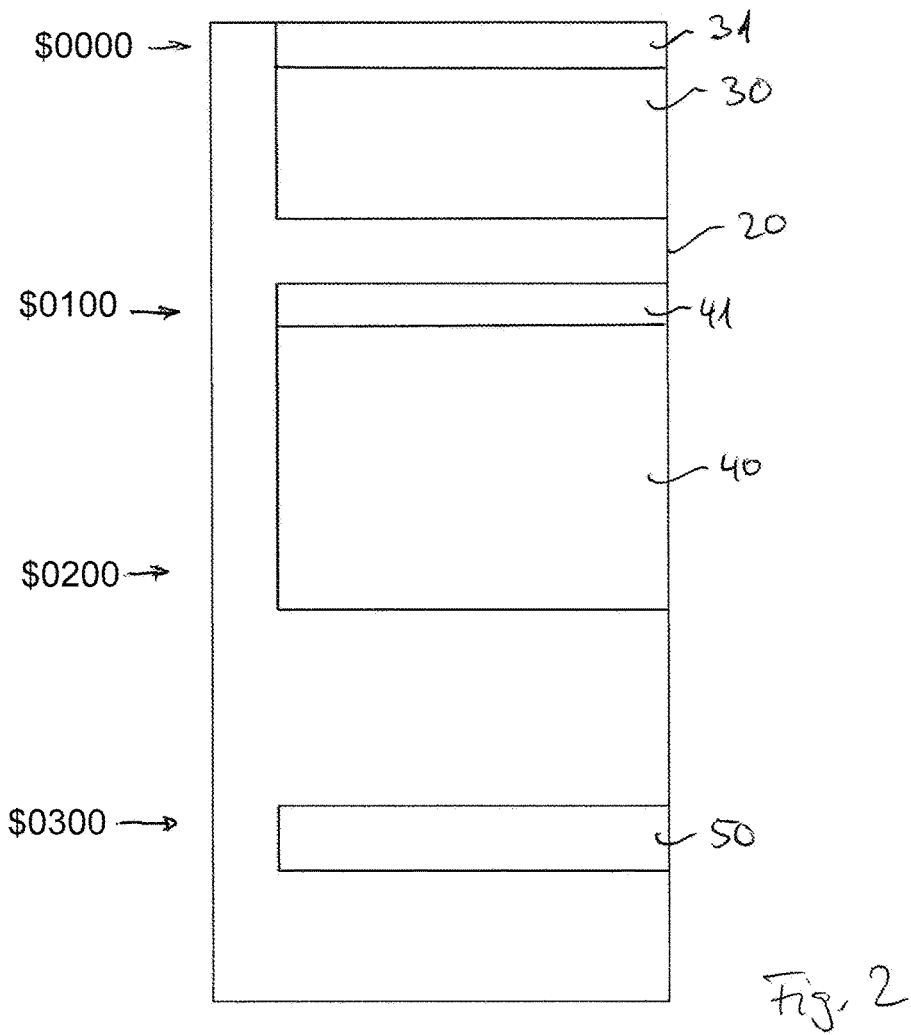

The configuration data is stored on the memory element 20 in a flexible data structure, which is shown schematically in FIG. 2. Therein, the logical content of the memory element 20 is shown with the memory address incrementing from top to bottom.

A first set 30 of configuration data is stored at a first memory address, for example at logical address $0000. A second set 40 of configuration data is stored after the first set 30, for example at logical address $0100. A termination data element 50 is placed in this case after the second set 40 of configuration data, for example at logical address $0300.

For better understanding, the logical addresses are specified in hexadecimal numbers ($ . . . ), so $0100 corresponds to a value of 256, $0200 to a value of 512, and so on.

The first set 30 of configuration data may be intended to be used with an older generation electrosurgical supply devices 10. Such supply devices expect only a single set of configuration data on memory element 20, which is always located at logical address $0000. This set of configuration data is limited in its content, as it can only contain parameters for electrosurgical instruments and waveforms that were already known when the corresponding generation of electrosurgical supply devices was developed.

For more recent instruments or waveforms, the second set 40 of configuration data is provided. A modern electrosurgical supply device 10 is capable of reading configuration data from other logical addresses of the memory element 20, and thus can access the second set 40 of configuration data.

The second set 40 of configuration data may store configuration data that supplements the configuration data of the first set 30, such that it can only be used in conjunction with that configuration data. Alternatively, the configuration data stored in the second set 40 may be complete in itself.

The logical address at which the second set 40 of configuration data is stored is dependent on the length of the first set 30 of configuration data. In this regard, the length of the first set 30 may be fixed and known, so that the logical address of the second set 40 is also known.

The first set 30 of configuration data may also be of variable length. In this case, the first set 30 includes a first length data element 31 indicating the length of the first set 30 and/or the address of the next set of configuration data.

The second set 40 of configuration data will typically always be of variable length and therefore also include a second length data element 41 indicating the length of the second set 40.

In addition to the first set 30 and the second set 40, any number of further sets of configuration data may be stored in the memory element 20. To indicate the end of the datasets, the termination data element 50 is placed after the last dataset.

The individual sets 30, 40 may be directly adjacent to each other. However, typically the memory element 20 will only be accessible for reading and/or writing in blocks, such as blocks of $0100 in length. Since the individual sets 30, 40 will not necessarily also be $0100 in length, there may be unused memory areas between individual sets 30, 40 or the termination data element 50.

Figure 3:
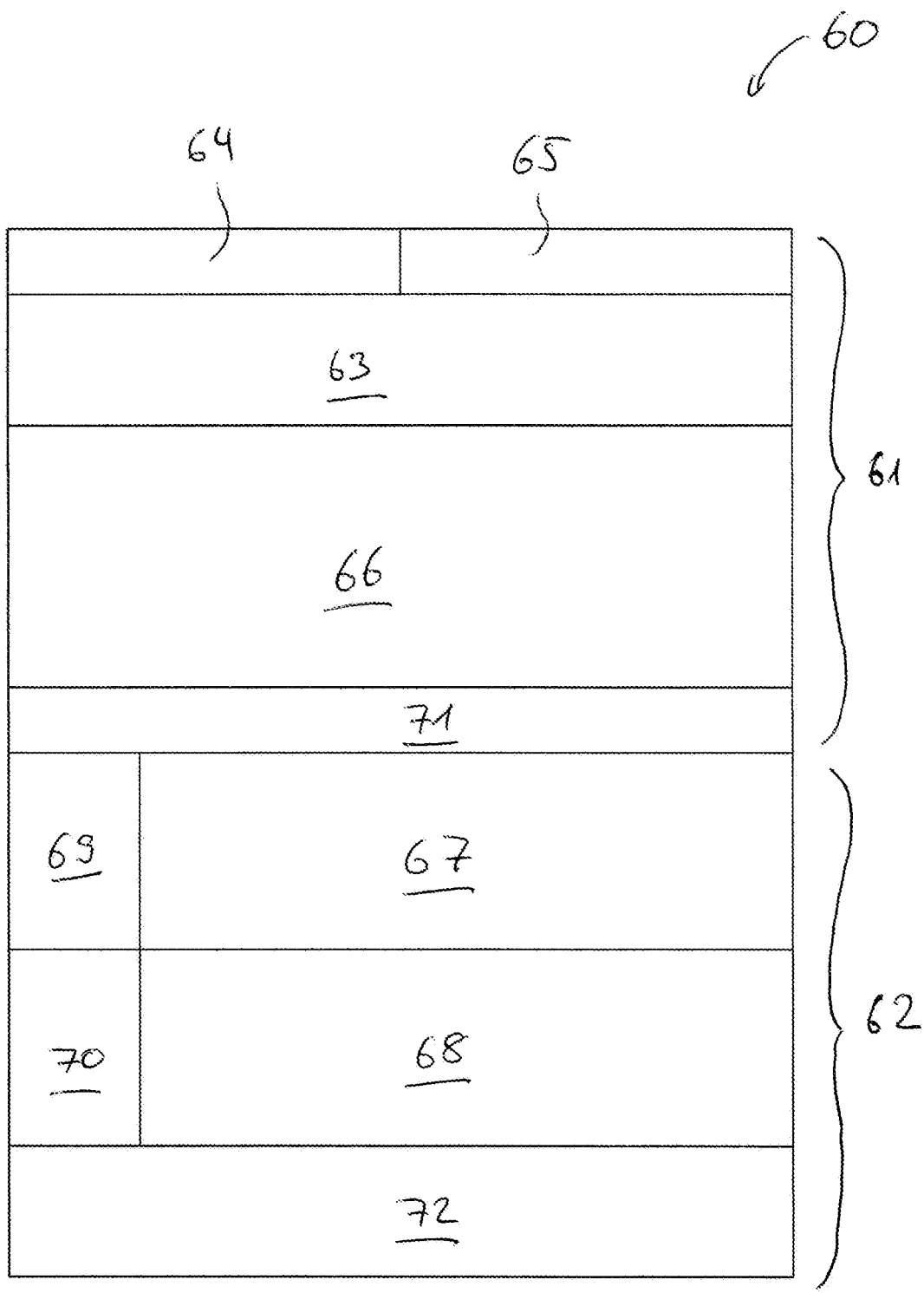

FIG. 3 shows in detail a possible structure of a dataset 60 of configuration data which may be stored in the data structure on the memory element 20 instead of or in addition to the sets 30, 40.

The dataset 60 has two sections 61, 62.

The first section 61 begins with a definition data element 63.

The definition data element 63 contains information about the structure of the dataset 60, i.e. type and/or version description, length and/or position information of this and other sections within the dataset 60, and/or position information of the next set of configuration data, as well as specific information of the memory element 20, such as the block size with which it can be read from or written to the memory element. In this regard, type and/or version data may be contained in a type data element 64, and length and/or position information may be contained in a length data element 65. The type data element 64 and/or the length data element 65 may be independent data elements or sub-elements of the definition data element 63.

Using the definition data element 63, the supply device 10 is able to determine whether it is compatible with the set of data 60.

If the dataset 60 is the last set of configuration data in the data structure, $0000 may be set in the definition data element 63 as the logical memory address of the next dataset.

The definition data element 63 defines the structure of both the parameter data element 66 and the further section 62.

The parameter data element 66 contains the actual configuration data for determining the electrical signal to be delivered by the supply device 10.

The section 61 of the dataset 60 of configuration data is defined as a "read only" section, meaning that the data stored in the section 61 cannot be operationally modified by the supply device 10.

The second section 62 includes two operational data elements 67, 68. Operational data of the electrosurgical instrument 11 is stored in the operational data elements 67, 68 by the electrosurgical supply device 10. This operational data may be consumption data, for example, number and duration of activations and/or delivered energy/power by the instrument 11, time stamps, temperature data, or the like. The operational data may be evaluated by the electrosurgical supply device 10 in order to determine whether further use of the instrument 11 is permissible.

In order to allow writing to the operational data elements 67, 68 by the supply device 10, the section 62 is defined as a "read/write" section, meaning that write access by the supply device 10 is allowed.

Since errors may occur when writing to the operational data elements 67, 68, for example due to interference signals, the operational data elements 67, 68 are written to alternately by the supply device 10. In this way, it is ensured that the operational data stored in the previous write access is still available if a write access has failed.

In order to determine which of the operational data elements 67, 68 contains the most recent operational data and which is to be written to next, a write flag 69, 70 is assigned to each of the operational data elements 67, 68. After a successful write operation to one of the operational data elements 67, 68, the assigned write flag 69 or 70 is toggled, i.e. set from "zero" to "one" or from "one" to "zero".

The supply unit 10 reads the write flags 69, 70 before each read or write access to the operational data elements 67, 68. If both write flags 69, 70 have the same value, the operational data in operational data element 67 is the most recent, and the next operational data is to be written to operational data element 68. On the other hand, if the write flags 69, 70 have different values, the operational data in the operational data element 68 is the most recent, and the next operational data is to be written to the operational data element 67.

In a factory-setting of the instrument 11, the sections 67, 68, 69 and 70 are set to a predetermined sequence of numbers, for example, the Fibonacci sequence. The supply unit 10 first attempts to recognize this sequence of numbers. If these sections contain this sequence, the supply device 10 recognizes that the instrument 11 is an unused instrument.

After the first use of the instrument 11, the supply device writes operational data to the operational data element 68, and sets the write flag 70 to the value "zero". The operational data may be usage data, for example, number and duration of activations and/or delivered energy/power by the instrument 11, timestamps, temperature data, or the like.

The next time the instrument 11 is used with the supply device 10 or with another supply device, it is now detected that the section 62 contains only the first half of the predetermined sequence of numbers, for example the Fibonacci sequence. As a result, the supply unit 10 knows that the most recent operational data is stored in the operational data element 68, and that the next operational data is to be written to the operational data element 67. The write flag 69 is set to the value "zero".

The next time the instrument 11 is used with the supply device 10, or with another supply device, the flags 69, 70 are read. Since their values are now the same, the supply unit knows that the most recent operational data is stored in operational data element 67, and that the next operational data is to be written to operational data element 68. The write flag 70 is set to the value "one". The next time the instrument 11 is used with the power supply unit 10, or with another supply unit, the flags 69, 70 are read again. Since their values are now not equal, the supply unit knows that the most recent operational data is stored in operational data element 68, and that the next operational data is to be written to operational data element 67.

Instead of two write flags 69, 70, a single write flag may also be used, which is toggled after each writing operation. The value of the write flag then indicates which operational data element contains the most recent operational data and which operational data element is to be written to next.

Defining individual areas of memory element 20 as "read only" or "read/write" is possible only for individual memory blocks of a predetermined size, which does not necessarily match the sizes of sections 61, 62. Therefore, unused memory areas 71, 72 may be present at the end of sections 61, 62. Similar unused memory elements, not shown, may be located between the individual data elements.

To ensure the integrity of the data stored in the single data elements, the data structure may include checksum elements, which are not shown.

Figure 4:
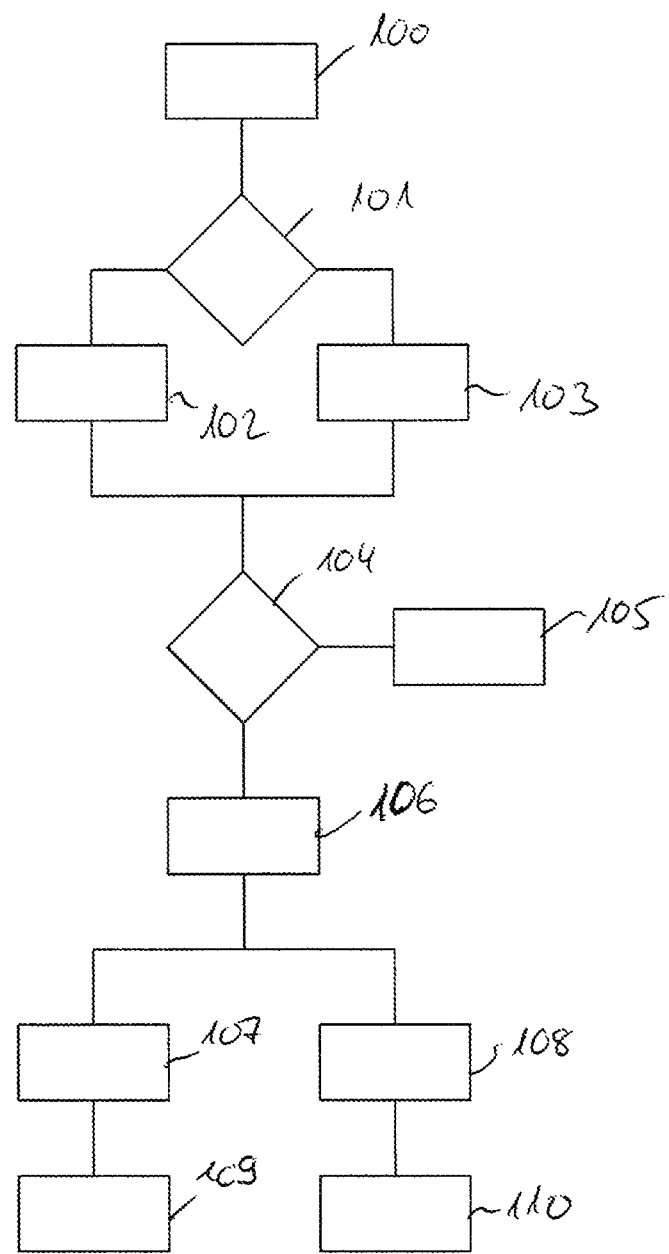

A method for reading and writing operational data by a supply device 10 is shown in FIG. 4. The write flags 69, 70 are read in a first step 100 and compared with each other in a second step 101. If both write flags 69, 70 have the same value, the operational data element 67 is read out in step 102. If the values of the write flags 69, 70 are different, the operational data element 68 is read out in step 103.

In step 104, the read operational data is used to check whether further use of the instrument 11 is permissible. If this is not the case, a corresponding message is issued by the supply device 10 in step 105, and the procedure is discontinued.

If use is permissible, the instrument 11 is activated by the supply device 10 in step 106, taking into account configuration data loaded from the memory element 20 and, if applicable, any user input.

After use, based on the result of the comparison in step 101, current operational data is either written to operational data element 68 in step 107 if the values of write flags 69, 70 were the same, or current operational data is written to operational data element 67 in step 108 if the values of write flags 69, 70 were different. After successful writing, the corresponding write flag 69 (step 109) or 70 (step 110) is toggled, thus completing the procedure.

In case the data structure contains multiple sets of configuration data comprising writable operational data elements, current operational data should be written to each set individually. This is the only way to ensure that a supply device which reads only a portion of the sets of configuration data also accesses the most recent operational data.

Figure 5:
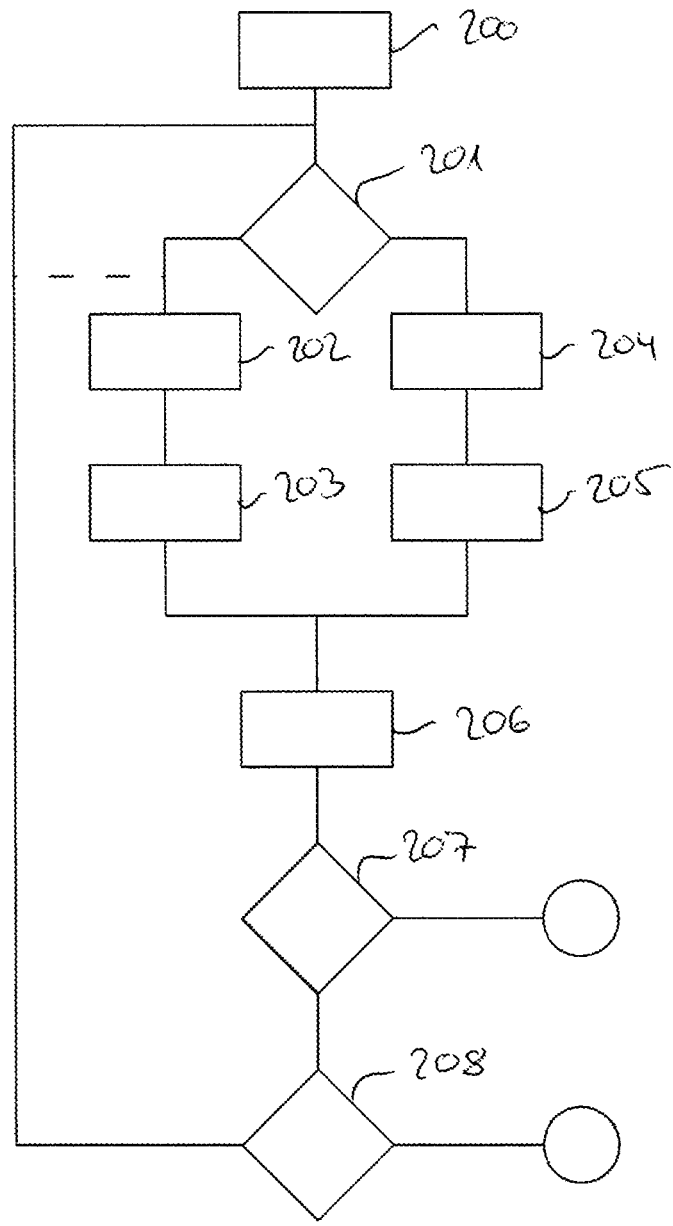

A method for reading the sets 30, 40, 60 of operational data from the memory element 20 by the supply device 10 is shown in FIG. 5. Herein, in a first step 200, a first block of data, starting at logical address $0000, is read from the memory element. In step 201, it is checked whether the read data block contains a length data element 31 of a first set 30 of configuration data. If so, in step 202 the complete first dataset 30 is read from memory 20, and in step 203 the logical memory address of the next set of configuration data is determined based on the contents of length data element 31.

If the first block of data does not contain a length data element, in step 204 the first dataset 30 is read assuming that it has a fixed known length. Accordingly, in step 205, the logical memory address of the next set of configuration data is determined based on the known fixed length of the first set 30.

Next, in a step 206, a data block is read from the previously determined next logical memory address, and in a step 207, a check is made to determine whether this data block contains meaningful data. If the corresponding data block does not contain meaningful data, all datasets are read from the memory element 20 and the method is terminated.

In the present example, the phrase "does not contain meaningful data" may include a case where the determined logical memory address is outside the accessible memory area of the memory element 20, for example, where the first set 30 of configuration data in an older generation electrosurgical instrument almost completely fills the memory element. In this case, the software implementing the described method must be capable of intercepting any memory address error that may occur.

Moreover, the phrase "does not contain meaningful data" includes any case in which the block of read data does not include either a type data element and/or a length data element of another set of configuration data, or a data termination element.

A next step 208 then examines whether the read data block includes a data termination element 50. In this case, all sets of configuration data are also read, and the procedure is terminated.

If, on the other hand, the data block contains a type data element and/or a length data element of another set of configuration data, the method is repeated from step 201. The procedure of step 201 may be omitted from the loop if all further sets of configuration data, except for the first set 30, always contain a length data element. In this case, it may be possible to jump directly to step 202 after step 208, as indicated by the dashed line in FIG. 5.

After completion of the procedure, the supply unit 10 can determine whether the respective sets are compatible with the supply unit 10 on the basis of the contents of the type data elements that were read and only consider such compatible sets.

The invention claimed is:

1. An electrosurgical system, comprising:
an electrosurgical supply device, and
an electrosurgical instrument, wherein
the electrosurgical instrument comprises a memory element which can be read out by the electrosurgical supply device when the electrosurgical instrument is connected to the electrosurgical supply device,
configuration data is stored on the memory element, which can be evaluated by the electrosurgical supply device in order to configure operating parameters which are compatible with the electrosurgical instrument,
the configuration data is arranged in a flexible data structure which allows the memory element to simultaneously store multiple sets of configuration data which can be read and evaluated by different types of electrosurgical supply devices,
the multiple sets of configuration data include a first set of configuration data compatible with an electrosurgical supply device of an older generation and a second set of configuration data compatible with an electrosurgical supply device of a more recent generation,
the first set of configuration data is configured to be read by the electrosurgical supply device when the electrosurgical supply device is the electrosurgical supply device of the older generation and when the electrosurgical supply device is the electrosurgical supply device of the more recent generation,
the second set of configuration data is configured to be read only by the electrosurgical supply device when the electrosurgical supply device is the electrosurgical supply device of the more recent generation, and the multiple sets of configuration data are configured to be read sequentially by the electrosurgical supply device when the electrosurgical supply device is the electrosurgical supply device of the more recent generation.

2. The electrosurgical system according to claim 1, wherein the first set of configuration data is stored at a fixed predetermined memory address of the memory element, and the second set of configuration data is stored at a second memory address of the memory element which is dependent on a length of the first set of configuration data.

3. The electrosurgical system according to claim 2, wherein a set of configuration data has a fixed predetermined length.

4. The electrosurgical system according to claim 2, wherein at least one set of configuration data has a flexible length, and comprises a length data element indicating a length of the corresponding set of configuration data and/or an address of a next set of configuration data.

5. The electrosurgical system according to claim 1, wherein the flexible data structure comprises a termination data element indicating an end of the flexible data structure.

6. The electrosurgical system according to claim 1, wherein the flexible data structure provides, for at least one set of configuration data, a memory area that cannot be operationally overwritten.

7. The electrosurgical system according to claim 1, wherein the flexible data structure provides, for at least one set of configuration data, a writable memory area, and the electrosurgical supply device is configured to store operational data in the writable memory area.

8. The electrosurgical system according to claim 7, wherein said writable memory area comprises two operational data elements, and the electrosurgical supply device is configured to store operational data alternately in one of the two operational data elements.

9. An electrosurgical instrument of an electrosurgical system, comprising:
   a memory element which can be read out by an electrosurgical supply device when the electrosurgical instrument is connected to the electrosurgical supply device, wherein
   configuration data is stored on the memory element, which can be evaluated by the electrosurgical supply device in order to configure operating parameters which are compatible with the electrosurgical instrument,
   the configuration data is arranged in a flexible data structure which allows the memory element to simultaneously store multiple sets of configuration data which can be read and evaluated by different types of electrosurgical supply devices, and
   the multiple sets of configuration data include a first set of configuration data compatible with an electrosurgical supply device of an older generation and a second set of configuration data compatible with an electrosurgical supply device of a more recent generation,
   the first set of configuration data is configured to be read by the electrosurgical supply device when the electrosurgical supply device is the electrosurgical supply device of the older generation and when the electrosurgical supply device is the electrosurgical supply device of the more recent generation,
   the second set of configuration data is configured to be read only by the electrosurgical supply device when the electrosurgical supply device is the electrosurgical supply device of the more recent generation, and
   the multiple sets of configuration data are configured to be read sequentially by the electrosurgical supply device when the electrosurgical supply device is the electrosurgical supply device of the more recent generation.

10. A method for reading the configuration data of the electrosurgical instrument in the electrosurgical system according to claim 1, comprising the steps of:
    a) determining an address at which the first set of configuration data is stored,
    b) reading a set of configuration data from the determined address,
    c) determining an address at which a next set of configuration data is expected,
    d) checking whether a termination data element is stored at the address determined in step c), and
    e) repeating steps b) to d) until the termination data element is detected at the determined address.

11. The method according to claim 10, wherein before step d) it is checked whether data is stored at the determined address, and the method is terminated if no data is stored at the determined address.

12. An electrosurgical supply device of an electrosurgical system, which is configured to perform a method for reading configuration data of an electrosurgical instrument in the electrosurgical system, the method comprising the steps of:
    a) determining an address at which a first set of configuration data compatible with an electrosurgical supply device of an older generation is stored,
    b) reading a set of configuration data from the determined address,
    c) determining an address at which a next set of configuration data compatible with an electrosurgical supply device of a more recent generation is expected,
    d) checking whether a termination data element is stored at the address determined in step c), and
    e) repeating steps b) to d) until the termination data element is detected at the determined address,
    wherein the first set of configuration data is configured to be read by the electrosurgical supply device when the electrosurgical supply device is the electrosurgical supply device of the older generation and when the electrosurgical supply device is an electrosurgical supply device of the more recent generation,
    the next set of configuration data is configured to be read only by the electrosurgical supply device when the electrosurgical supply device is the electrosurgical supply device of the more recent generation, and
    the first set of configuration data and next second set of configuration data are configured to be read sequentially by the electrosurgical supply device when the electrosurgical supply device is the electrosurgical supply device of the more recent generation.

13. The electrosurgical system according to claim 1, wherein the second set of configuration data is not compatible with the electrosurgical supply device of the older generation.

14. The electrosurgical system according to claim 1, wherein the second set of configuration data supplements the first set of configuration data and is used in conjunction with the first set of configuration data.

* * * * *